United States Patent
Park et al.

(10) Patent No.: US 9,610,306 B2
(45) Date of Patent: Apr. 4, 2017

(54) PHARMACEUTICAL COMPOSITION COMPRISING SILKWORM AS AN ACTIVE INGREDIENT FOR PREVENTION AND TREATMENT OF TISSUE INJURY BY RADIATION

(71) Applicant: KOREA ATOMIC ENERGY RESEARCH INSTITUTE, Daejeon (KR)

(72) Inventors: Sang Hyun Park, Jeongeup-si (KR); Beom Su Jang, Daejeon (KR); YouRee Nam, Jeongeup-si (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 15/076,352

(22) Filed: Mar. 21, 2016

(65) Prior Publication Data

US 2016/0199420 A1 Jul. 14, 2016

Related U.S. Application Data

(63) Continuation of application No. PCT/KR2014/006613, filed on Jul. 21, 2014.

(30) Foreign Application Priority Data

Oct. 8, 2013 (KR) .......................... 10-2013-0120099

(51) Int. Cl.
A61K 35/64 (2015.01)

(52) U.S. Cl.
CPC .................................. *A61K 35/64* (2013.01)

(58) Field of Classification Search
None
See application file for complete search history.

(56) References Cited

FOREIGN PATENT DOCUMENTS

IN 200800365 I4 * 9/2009
KR 10-2013-0035671 4/2013

OTHER PUBLICATIONS

Lee (Int. J. Mol. Sci. (2011), vol. 12, pp. 4456-4464).*
Yu (PLOS ONE (Jun. 2013), vol. 8, No. 6, e68746, pp. 1-11).*
International Search Report from parent PCT Application No. PCT/KR2014/006613, 4 pages (mailed Oct. 30, 2014).
Park et al., "Effect of Silkworm Hemolymph on Oxidative Stress Induced by UVA and Hydrogen Peroxide in Fibroblasts," *Proceeding of Current Biotechnology and Bioengineering(XVII)*. Jinju: KSBB (2005).
Written Opinion from parent PCT Application No. PCT/KR2014/006613, 6 pages (mailed Oct. 30, 2014).

* cited by examiner

*Primary Examiner* — Susan Hoffman
(74) *Attorney, Agent, or Firm* — Klarquist Sparkman, LLP

(57) ABSTRACT

The present invention relates to a pharmaceutical composition for the prevention and treatment of tissue injury caused by irradiation which comprises silkworm hemolymph as an active ingredient. Particularly, when the silkworm hemolymph of the present invention was administered to an animal model with liver damage induced by irradiation, plasma AST and liver MDA were significantly decreased, indicating that the silkworm hemolymph of the invention can be effectively used as a composition for the prevention and treatment of disease caused by the exposure on radiation including tissue injury caused by irradiation, etc.

6 Claims, 1 Drawing Sheet

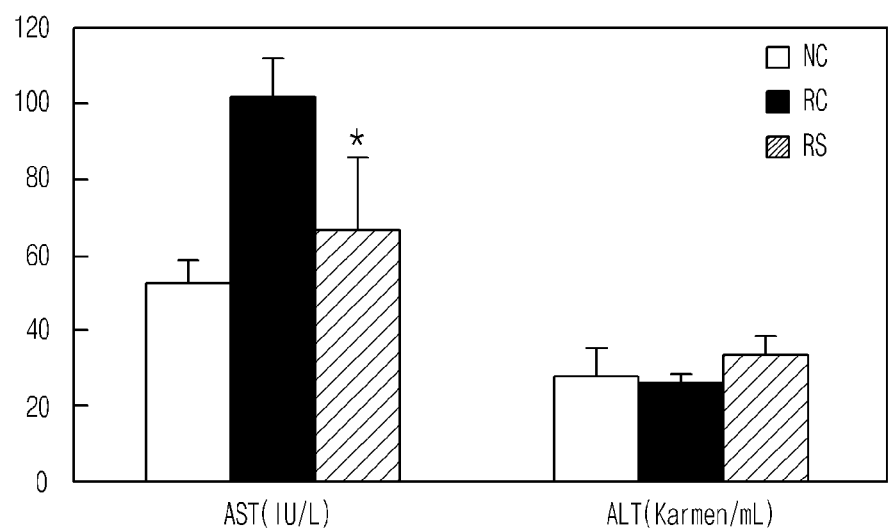

PHARMACEUTICAL COMPOSITION COMPRISING SILKWORM AS AN ACTIVE INGREDIENT FOR PREVENTION AND TREATMENT OF TISSUE INJURY BY RADIATION

CROSS REFERENCE TO RELATED APPLICATIONS

This is a continuation of PCT Application No. PCT/KR2014/006613, filed on Jul. 21, 2014, which is incorporated by reference, and which claims priority to Korean Application No. 10-2013-0120099, filed on Oct. 8, 2013.

TECHNICAL FIELD

The present invention relates to a pharmaceutical composition comprising silkworm (*Bombyx mori* L.) hemolymph as an active ingredient for the prevention and treatment of tissue injury caused by irradiation.

BACKGROUND

Silkworm (*Bombyx mori* L.) is a larva belonging to Bombycidae which was first recorded in <Sinnongbonchogyeong( 神農本草經 )>. Silkworm powder has been widely used for diabetics in folk remedy. It was confirmed by animal test and clinical test that silkworm powder had the activity of lowering blood sugar by inhibiting the activity of intestinal α-glucosidase and also had the activities of alleviating hepatitis and liver cirrhosis and of inhibiting the generation of ROS (reactive oxygen species) and of increasing the activity of ROS scavenger enzyme. In addition to the studies on silkworm powder, studies about various effects of hydrolysates of silkworm cocoon such as fibroin and silk sericin confirmed that such hydrolysates also had the activities of suppressing ROS in liver tissues, anti-diabetes, lowering blood cholesterol, and alcoholysis, etc. Silkworm is an insect that has a relatively big body volume, suggesting that it is easy to obtain hemolymph therefrom. Moreover, chemical composition of silkworm hemolymph is simpler and well-studied (Higashihash et al., 1991), compared with FBS (fetal bovine serum), so that it favors for the separation and purification of useful materials from cells. Well preserved genealogical characteristics is also advantage of silkworm hemolymph, suggesting that there is hardly difference in between lots as long as it is produced from the same silkworm genealogy.

According to the recent development in industry and in modern medicine, radiation and radioisotope are widely being used. As national income increases, the interest in personal health is also increased. Accordingly the use of radiation in the field of medicine is increased as well. In particular, radiation and radioisotope have been widely used in diagnosis and treatment of diseases in the field of medicine, which might affect health of patients and radiation handling workers. Radiation increases reactive oxygen species (ROS) in the inside of human body and the increased ROS results in the damage of DNA, protein, and cell membrane and further affects hematopoiesis system. So, studies and attempts to develop radioprotective agents are actively under-going. As radioprotective agents to prevent biological damage caused by radiation, such synthetic materials as WR-2721 (amifostine) and WR-638 (aminoethylphosphorothioate) have been developed. However, they demonstrate a strong toxicity and are highly expensive. Therefore, it is strongly requested to develop a natural radioprotective agent with less side effects.

SUMMARY

In the course of study to find out a natural radioprotective agent which is safe with no toxicity, the present inventors confirmed that when silkworm hemolymph was administered to an animal model with liver damage caused by irradiation, plasma AST and liver MDA were significantly reduced, indicating a significant alleviation of liver damage, leading to the completion of this invention by further confirming that silkworm hemolymph, therefore, could be effectively used for the prevention and treatment of tissue injury caused by irradiation.

Technical Problem

It is an object of the present invention to provide a pharmaceutical composition comprising silkworm (*Bombyx mori* L.) hemolymph as an active ingredient for the prevention and treatment of tissue injury caused by irradiation.

Technical Solution

To achieve the above object, the present invention provides a pharmaceutical composition comprising silkworm (*Bombyx mori* L.) hemolymph as an active ingredient for the prevention and treatment of tissue injury caused by irradiation.

The present invention also provides a health food for the prevention and improvement of tissue injury caused by irradiation which comprises silkworm hemolymph as an active ingredient.

The present invention further provides a radioprotective composition comprising silkworm hemolymph as an active ingredient.

The present invention also provides a method for the prevention and treatment of tissue injury caused by irradiation containing the step of administering a pharmaceutically effective dose of silkworm hemolymph to a subject.

The present invention also provides a radiation protection method containing the step of administering a pharmaceutically effective dose of silkworm hemolymph to a subject.

The present invention also provides a use of silkworm hemolymph as a composition for the prevention and treatment of tissue injury caused by irradiation.

The present invention also provides a use of silkworm hemolymph for the preparation of a health food for the prevention and improvement of tissue injury caused by irradiation.

In addition, the present invention provides silkworm hemolymph as a radioprotective composition.

Advantageous Effect

The present invention relates to a pharmaceutical composition for the prevention and treatment of tissue injury caused by irradiation which comprises silkworm hemolymph as an active ingredient. More particularly, when silkworm hemolymph was administered to an animal model having liver damage caused by irradiation, plasma AST and liver MDA were significantly reduced, indicating the liver damage was alleviated. Therefore, the said silkworm hemolymph can be effectively used as a composition for the prevention and treatment of disease caused by the exposure on radiation including tissue injury by irradiation.

DESCRIPTION OF DRAWINGS

The application of the preferred embodiments of the present invention is best understood with reference to the accompanying drawings, wherein:

FIG. 1 is a diagram illustrating the effect of silkworm hemolymph on plasma AST and ALT in an animal model with liver damage caused by irradiation, observed after administering the silkworm hemolymph to the mouse model:

☐: normal control (NC);
■: radiation control (RC); and
▨: radiation+silkworm hemolymph (RS).

DETAILED DESCRIPTION

Hereinafter, the present invention is described in detail.

The present invention provides a pharmaceutical composition for the prevention and treatment of tissue injury caused by irradiation which comprises silkworm (*Bombyx mori* L.) hemolymph as an active ingredient.

The said silkworm hemolymph is the fluid that supplies nutrients to the insect itself, *Bombyx mori* L. The body fluid obtained by wounding abdominal legs of silkworm or the body fluid obtained by performing mechanical press extraction with silkworm can be used. According to the blood collecting method, the silkworm hemolymph obtained by using small scale blood collecting and the silkworm hemolymph obtained by using large scale blood collecting can also be used. As for the small scale blood collecting, wound is made on abdominal legs of silkworm at the third day of $5^{th}$ instar larvae. The body fluid is collected from the wound on ice, which is heat-treated and centrifuged thereafter to obtain supernatant. The obtained supernatant is used as the silkworm hemolymph. The large scale blood collecting is the method comprising the following steps: silkworm at the third day of $5^{th}$ instar larvae is frozen; the frozen silkworm is dissected and the midgut is removed; centrifugation is performed to obtain supernatant; and the obtained supernatant is used as the silkworm hemolymph. Or the large scale blood collecting method can also be composed of the following steps: wound is made on the head, tail, and abdominal legs of silkworm; centrifugation is performed to obtain supernatant; the supernatant is heat-treated; centrifugation is performed again to obtain supernatant; and the obtained supernatant is used as the silkworm hemolymph.

The radiation herein is preferably selected from the group consisting of gamma ray, electron beam, UV, and X ray, but not always limited thereto.

The said tissue herein is preferably one or more tissues selected from the group consisting of liver, skin, gastrointestinal track, and respiratory system, but not always limited thereto.

In a preferred embodiment of the present invention, the present inventors constructed liver damaged mice by irradiation. Wound was made on abdominal legs of silkworm at the third day of $5^{th}$ instar larvae, followed by collecting the body fluid. To prevent blackening, the obtained body fluid was heat-treated and supernatant was obtained therefrom, which was administered to the liver damaged mice.

To investigate the effect of silkworm hemolymph on the spleen and body weight of the mouse model with liver damage caused by irradiation, the inventors administered silkworm hemolymph to the liver damaged mouse model and measured the spleen index and body weight. As a result, the spleen indexes of both the radiation control group (RC) and the radiation+silkworm hemolymph group (RS) were decreased, compared with that of the normal control group (NC), and the weight of RS was increased, compared with that of RC, suggesting that the silkworm hemolymph relieved weight loss according to the tissue injury by irradiation (see Table 1).

To investigate the effect of silkworm hemolymph on hepatocytes of the mouse model with liver damage caused by irradiation, the inventors performed plasma aspartate aminotransferase (AST) and alanine aminotransferase (ALT) assay after administering silkworm hemolymph to the mouse model with liver damage caused by irradiation. As a result, AST was increased in RC but significantly decreased in RS, suggesting that the silkworm hemolymph of the present invention had protective effect on oxidative hepatocyte damage caused by irradiation (see FIG. 1).

To investigate the effect of silkworm hemolymph on liver damage caused by irradiation, the present inventors administered silkworm hemolymph to the mouse model with liver damage caused by irradiation and then performed lipid peroxide test with the liver tissue. As a result, the content of malondialedhyde (MDA), the index of lipid peroxidation, was significantly decreased in RS, compared with that in RC, indicating that the silkworm hemolymph could inhibit lipid peroxidation in liver tissue so as to alleviate the liver damage caused by irradiation (Table 2).

The administration of the silkworm hemolymph of the present invention significantly reduced plasma AST and liver MDA in the animal model with liver damage caused by irradiation, suggesting that the silkworm hemolymph had liver damage alleviating effect. Therefore, the silkworm hemolymph of the present invention can be effectively used as a composition for the prevention and treatment of tissue injury caused by irradiation.

The present invention also provides a health food comprising silkworm hemolymph as an active ingredient for the prevention and treatment of tissue injury caused by irradiation.

The radiation herein is preferably selected from the group consisting of gamma ray, electron beam, UV, and X ray, but not always limited thereto.

The said tissue herein is preferably one or more tissues selected from the group consisting of liver, skin, gastrointestinal track, and respiratory system, but not always limited thereto.

The administration of the silkworm hemolymph of the present invention significantly reduced plasma AST and liver MDA in the animal model with liver damage caused by irradiation, suggesting that the silkworm hemolymph had liver damage alleviating effect. Therefore, the silkworm hemolymph of the present invention can be effectively used as a health food for the prevention and improvement of tissue injury caused by irradiation.

For the health food of the present invention, the silkworm hemolymph of the invention can be used as a food additive. In that case, the silkworm hemolymph of the present invention can be added as it is or as mixed with other food components according to the conventional method.

The food herein is not limited. For example, the silkworm hemolymph of the present invention can be added to meats, sausages, breads, chocolates, candies, snacks, cookies, pizza, ramyuns, flour products, gums, dairy products including ice cream, soups, beverages, alcohol drinks and vitamin complex, etc, and in wide sense, almost every food applicable in the production of health food can be included.

The silkworm hemolymph of the present invention can be used as a food additive. In that case, the silkworm hemolymph of the present invention can be added as it is or as mixed with other food components according to the conventional method. The mixing ratio of active ingredients can be regulated according to the purpose of use (prevention or improvement). In general, to produce health food or beverages, the silkworm hemolymph of the present invention is preferably added by 0.01~15 weight % by the total weight of the food or beverages, for example it is preferably added by 0.02~5 g and more preferably 0.3~1 g to 100 ml of health beverages. However, if long term administration is required for health and hygiene or regulating health condition, the content can be lower than the above but higher content can be accepted as well since the silkworm hemolymph of the present invention has been proved to be very safe.

The health beverages containing the silkworm hemolymph of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xylytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent.

In addition to the ingredients mentioned above, the food of the present invention can include in a variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The silkworm hemolymph of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0~20 weight part per 100 weight part of the silkworm hemolymph of the invention.

The present invention also provides a radioprotective composition comprising silkworm hemolymph as an active ingredient.

The administration of the silkworm hemolymph of the present invention significantly reduced plasma AST and liver MDA in the animal model with liver damage caused by irradiation, suggesting that the silkworm hemolymph had liver damage alleviating effect. Therefore, the silkworm hemolymph of the present invention can be effectively used as a radioprotective composition.

The composition of the present invention can be used as a pharmaceutical composition for the prevention or treatment of tissue injury caused by irradiation. The radioprotective composition of the present invention can include a pharmaceutically effective dose of silkworm hemolymph alone or together with one or more pharmaceutically acceptable carriers, excipients, or diluents.

The term "pharmaceutically effective dose" herein indicates the amount of the said bioactive constituent enough to bring a wanted physiological or pharmaceutical activity when administered to an animal or human. However, the pharmaceutically effective dose can be regulated according to the age, weight, health condition, and gender of patient, and administration pathway, and treatment period, etc.

The pharmaceutically effective dose of the silkworm hemolymph of the present invention is 0.5~100 mg/day/weight (kg), and preferably 0.5~5 mg/day/weight (kg). However, the said pharmaceutically effective dose can be adjusted according to age, weight, health condition, and gender of patient, administration pathway, and treatment period, etc.

The term "pharmaceutically acceptable" herein indicates that a compound is physiologically acceptable and when it is administered to human, general allergic reaction including gastrointestinal disorder and dizziness or similar reaction to such allergic reaction is not induced. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silcate, cellulose, methyl cellulose, microcrystalline cellulose, polyvinyl pyrrolidone, water, methylhydroxybenzoate, propylhydroxybenzoate, talc, magnesium stearate and mineral oil. Fillers, anticoagulants, lubricants, wetting agents, flavors, emulsifiers, and antiseptics can also be added thereto.

The composition of the present invention can be formulated according to the conventional method informed to those in the art in order for the composition to release its active ingredient fast, continuously, and for a long time. The composition of the present invention can be prepared for oral or parenteral administration. The formulation is exemplified by powder, granule, tablet, emulsion, syrup, aerosol, soft or hard gelatin capsule, sterilized injection, and sterilized powder.

The representative formulation for parenteral administration is injectable solution. The injectable solution is preferably isotonic solution or suspension. The injectable solution can be prepared according to the conventional method known to those in the art by using a proper dispersant or wetting agent, and suspending agent. For example, each active ingredient is dissolved in saline or buffer, leading to the preparation of the injectable solution. The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrrolidone, and if necessary disintegrating agents such as starch, agarose, alginic acid or its sodium salt or azeotropic mixtures and/or absorbents, coloring agents, flavors, and sweeteners can be additionally included therein. The formulations above can be prepared by the conventional methods for mixing, granulating, or coating process.

The composition of the present invention can additionally contain antiseptics, wettable powders or emulsifiers, salts or buffers for the regulation of osmotic pressure, and other therapeutically useful materials, and the composition can be formulated by the conventional method.

The radioprotective composition of the present invention can be administered by various pathways such as oral administration, transdermal administration, hypodermic administration, intravenous administration, or intramuscular administration. The dose of the active ingredient can be determined according to administration pathway, age, gender, and weight of patient, and severity of disease, etc. The composition of the present invention can be co-administered with generally informed compounds capable of increasing the effect.

The administration pathways for the composition of the present invention are exemplified by oral administration and parenteral administration including intravenous administration, hypodermic administration, intranasal administration, or intraperitoneal administration. The composition of the present invention can be administered to both human and animal by oral or parenteral administration. The oral administration can include sublingual application. The parenteral administration herein is exemplified by injections such as hypodermic injection, intramuscular injection and intravenous injection, and dripping method.

The present invention also provides a method for the prevention of tissue injury caused by irradiation which comprises the step of administering a pharmaceutically effective dose of silkworm hemolymph to a subject.

The present invention also provides a method for the treatment of tissue injury caused by irradiation which comprises the step of administering a pharmaceutically effective dose of silkworm hemolymph to a subject.

The present invention also provides a radioprotective method which comprises the step of administering a pharmaceutically effective dose of silkworm hemolymph to a subject.

The radiation herein is preferably selected from the group consisting of gamma ray, electron beam, UV, and X ray, but not always limited thereto.

The said tissue herein is preferably one or more tissues selected from the group consisting of liver, skin, gastrointestinal track, and respiratory system, but not always limited thereto.

The administration of the silkworm hemolymph of the present invention significantly reduced plasma AST and liver MDA in the animal model with liver damage caused by irradiation, suggesting that the silkworm hemolymph had liver damage alleviating effect. Therefore, the silkworm hemolymph of the present invention can be effectively used for the prevention and treatment of tissue injury caused by irradiation.

The present invention also provides silkworm hemolymph to be used as a composition for the prevention and treatment of tissue injury caused by irradiation.

The present invention also provides silkworm hemolymph to be used as a health food for the prevention and improvement of tissue injury caused by irradiation.

In addition, the present invention provides silkworm hemolymph to be used as a radioprotective composition.

The radiation herein is preferably selected from the group consisting of gamma ray, electron beam, UV, and X ray, but not always limited thereto.

The said tissue herein is preferably one or more tissues selected from the group consisting of liver, skin, gastrointestinal track, and respiratory system, but not always limited thereto.

The administration of the silkworm hemolymph of the present invention significantly reduced plasma AST and liver MDA in the animal model with liver damage caused by irradiation, suggesting that the silkworm hemolymph had liver damage alleviating effect. Therefore, the silkworm hemolymph of the present invention can be effectively used as a composition for the prevention and treatment of tissue injury caused by irradiation, as a health food for the improvement thereof, and as a radioprotective composition.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Construction of Animal Model with Liver Damage Caused by Irradiation

<1-1> Extraction of Silkworm Hemolymph

Silkworm was purchased from Taeyang farm at Yeongdeok, Gyeongsangbuk-do, Korea. Silkworm was fasted for 12 hours and then silkworm hemolymph was obtained by wounding abdominal legs of the insect with a needle. The obtained hemolymph was heated at 60~65° C. for 30 minutes to prevent blackening, followed by centrifugation at 12,000 rpm for 1 hour. Then, the supernatant was used for the experiment.

<1-2> Construction of Animal Model with Liver Damage Caused by Irradiation

To prepare an animal model with liver damage caused by irradiation, 15 female Balb/c mice at 5 weeks of age were purchased from Orient, Colo. Ltd. (Iksan, Jeollabuk-do, Korea). The animals were adapted in a raising cage at the temperature of 23±2° C., humidity of 50±5%, with 12 hour dark/light cycle for a week, during which solid feeds and drinking water were given freely. The mice were grouped 5 random mice with similar average body weight per each group; the normal control group (NC), the radiation control group (RC), and radiation+silkworm hemolymph group (RS). Except the NC, the mice of other two groups were placed in an acrylic box, which were irradiated with 6 Gy of gamma ray at the dose rate of 1.1 Gy/min by using Gammacell 40 Exactor (MDS Nordion, Canada) at Advanced Radiation Technology Institute (ARTI), Korea Atomic Energy Research Institute(KAERI).

<1-3> Treatment of Silkworm Hemolymph

The NC and RC mice, prepared in Example <1-2>, were administered with saline, while the RS mice were orally administered with the silkworm hemolymph obtained by the method of Example <1-1> at the dose of 5 ml/weight kg. The administration of saline and silkworm hemolymph was executed once a day for 7 days. One hour after the final administration, the animals were sacrificed. All the test animals were fasted at least 12 hours before being sacrificed.

Example 1

Effect of Silkworm Hemolymph on the Spleen and Weight of the Mouse with Liver Damage Caused by Irradiation To investigate the effect of silkworm hemolymph on the spleen and weight of the mouse with liver damage induced by irradiation, the spleen index and body weight were measured.

Precisely, the mice of NC, RC, and RS, prepared in Example <1-3>, were anesthetized by general inhalational anesthesia with isoflurane. Then, the abdomens of the mice were opened and the spleens were obtained. The spleens were washed with saline and then blood was removed by using an absorbent paper, followed by weighing. Then, the spleen index was calculated by the below [Mathematical Formula 1]. The results obtained from the measurement were statistically analyzed by using SPSS/Windows 18.0. The mean value and standard deviation (Mean±SD) for 5 mice per each group were calculated. To investigate the difference in average among the said three groups, one-way ANOVA was performed. Difference in variables was examined by Duncan's multiple range test. All the statistical significances were examined at $\alpha=0.05$.

Mathematical Formula 1

Spleen Index=Spleen Weight/Body Weight×100

As a result, as shown in Table 1, there was no significant difference in the spleen index between RC and RS, but there was a big difference between these two groups and NC, indicating that tissue injury was induced by irradiation in both RC and RS mice. From the measurement of weight, it was confirmed that there was no statistic significance among those three groups but the weight of RS mouse was comparatively increased, compared with that of RC. Thus, the silkworm hemolymph was confirmed to prevent weight loss over the tissue injury caused by irradiation (Table 1).

TABLE 1

Effect of silkworm hemolymph treatment on spleen index and body weight of mice exposed to γ-irridation

| Group[a] | Spleen index | Body weight(g) |
|---|---|---|
| NC | 0.40 ± 0.06* | 17.94 ± 0.83 |
| RC | 0.12 ± 0.01 | 16.64 ± 0.72 |
| RS | 0.12 ± 0.01 | 17.64 ± 0.79 |

*$p < 0.05$, compared with RC
[a] NC: Control rats administered with the vehicle alone
RC: mice exposed to γ-irridation and treated with vehicle
RS: mice exposed to γ-irridation and treated with 5 ml/kg BW of silkworm hemolymph Example 3

Effect of Silkworm Hemolymph on Hepatocytes of the Mouse with Liver Damage Induced by Irradiation The increases of aspartate aminotransferase (AST) and alanine aminotransferase (ALT) is known as the index for hepatocyte destruction (Hsu H Y et al. 1990; Ohta S, et al. 1990). To investigate the effect of silkworm hemolymph on hepatocytes of the mouse with liver damage induced by irradiation, plasma AST and ALT of the mouse administered with silkworm hemolymph after being irradiated were examined.

Particularly, the mice of each NC, RC, and RS group prepared by the manner described in Example <1-3> were anesthetized by general inhalational anesthesia with isoflurane. The abdomens of the mice were opened and then blood was taken from the postcaval vein in the tube treated with heparin. The tube was centrifuged at 5,000 rpm for 10 minutes and the obtained supernatant, the plasma, was used for the test. Plasma AST and ALT were measured by the method of Bergmeye (1978). Briefly, each substrate solution L-asparaginic acid and DL-alanine was placed in the tube, which stood at 37° C. for 5 minutes. Then, plasma was added thereto, which stood at 37° C. for 60 minutes (AST) and for 30 minutes (ALT). Chromogenic reagent was added thereto, which stood again at room temperature for 5 minutes. The reaction was terminated by adding 0.4N NaOH solution and $OD_{505}$ was measured. The result was calculated by using lithium pyruvate as a standard. The values obtained from the calculation were statistically treated as shown in Example 2.

As a result, as shown in FIG. 1, it was confirmed that there was no statistical significance in ALT among NC, RC, and RS. AST is the enzyme mediating transamination between amino acid and α-keto acid, which is largely distributed in the liver. Particularly in patients with acute hepatitis, blood AST is rapidly increased. It was confirmed that AST was increased in RC but significantly decreased in RS, suggesting that the silkworm hemolymph of the present invention had protective effect on oxidative hepatocyte damage caused by irradiation (FIG. 1).

Example 4

Effect of Silkworm Hemolymph on Liver Tissue of the Mouse with Liver Damage Induced by Irradiation To investigate the effect of silkworm hemolymph on liver damage of the mouse with liver damage caused by irradiation, lipid peroxide test was performed with the liver tissue obtained from the mouse administered with silkworm hemolymph after being irradiated.

Particularly, the mice of each NC, RC, and RS group prepared by the manner described in Example <1-3> were anesthetized by general inhalational anesthesia with isoflurane. The abdomens of the mice were opened and the liver tissue was extracted. The obtained liver tissue was washed with saline to remove blood.

To measure the content of malondialedhyde (MDA), the index for lipid peroxidation, in the liver tissue of each NC, RC, and RS mouse, MDA quantification kit (Cell Biolabs, USA) was used according to the manufacturer's instruction. MDA content was presented as μmole per mg of protein. Protein content in the liver tissue was measured by the method of Bradford (1976) using bovine serum albumin as a standard. The results were statistically treated as shown in Example 3.

As a result, as shown in Table 2, MDA content was significantly lower in RS than in RC, suggesting that the silkworm hemolymph of the present invention inhibited lipid peroxidation in the liver tissue so as to protect the liver from being damaged by irradiation (Table 2).

TABLE 2

Effect of silkworm hemolymph treatment on the status of MDA in the liver tissue of mice exposed to γ-irridation

| Group | MDA((μmole/mg protein) |
|---|---|
| NC | 33.21 ± 7.02 |
| RC | 39.64 ± 7.95 |
| RS | 25.27 ± 1.70* |

*$p < 0.05$, compared with RC

The Manufacturing Examples for the composition of the present invention are described hereinafter.

Manufacturing Example 1

Preparation of Pharmaceutical Formulation Containing Silkworm Hemolymph as an Active Ingredient <1-1> Preparation of Powders

| | |
|---|---|
| Silkworm hemolymph | 2 g |
| Lactose | 1 g |

Powders were prepared by mixing all the above components, which were filled in airtight packs according to the conventional method for preparing powders.

<1-2> Preparation of Tablets

| | |
|---|---|
| Silkworm hemolymph | 100 mg |
| Corn starch | 100 mg |
| Lactose | 100 mg |
| Magnesium stearate | 2 mg |

Tablets were prepared by mixing all the above components by the conventional method for preparing tablets <1-3> Preparation of Capsules

| | |
|---|---|
| Silkworm hemolymph | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Silkworm hemolymph | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Silkworm hemolymph | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Food Containing Silkworm Hemolymph as an Active Ingredient

Foods containing the silkworm hemolymph of the present invention were prepared as follows.

<2-1> Preparation of Flour Food 0.5~5.0 weight part of the silkworm hemolymph of the present invention was added to the flour. Foods such as bread, cake, cookies, crackers and noodles were prepared with the flour mixture according to the conventional method.

<2-2> Preparation of Soups and Gravies 0.1~5.0 weight part of the silkworm hemolymph of the present invention was added to soups and gravies. Health enhancing meat products, soups and gravies were prepared with this mixture by the conventional method.

<2-3> Preparation of Ground Beef

Health enhancing ground beef was prepared by mixing 10 weight part of the silkworm hemolymph of the present invention with ground beef according to the conventional method.

<2-4> Preparation of Dairy Products

5~10 weight part of the silkworm hemolymph of the present invention was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The silkworm hemolymph of the present invention was concentrated under reduced pressure, spray-dried and pulverized to obtain 60-mesh dry powders.

Sun-Sik was prepared by mixing the dry powders of the grains, seeds and the silkworm hemolymph of the present invention according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), The silkworm hemolymph of the present invention (3 weight part),

*Ganoderma lucidum* (0.5 weight part),

*Rehmannia glutinosa* (0.5 weight part)

Manufacturing Example 3

Preparation of Health Beverages Containing Silkworm Hemolymph as an Active Ingredient <3-1> Preparation of Health Beverages The silkworm hemolymph of the present invention (5 g) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<3-2> Preparation of Vegetable Juice

Health enhancing vegetable juice was prepared by adding 5 g of the silkworm hemolymph of the present invention to 1,000 ml of tomato or carrot juice according to the conventional method.

<3-3> Preparation of Fruit Juice

Health enhancing fruit juice was prepared by adding 1 g of the silkworm hemolymph of the present invention to 1,000 ml of apple or grape juice according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for the treatment of liver tissue injury that has been caused by irradiation comprising the step of administering a pharmaceutically effective dose of silkworm hemolymph to a subject with liver tissue injury that has been caused by irradiation.

2. The method for the treatment of tissue injury that has been caused by irradiation according to claim 1, wherein the radiation comprises gamma ray, electron beam, UV, or X ray.

3. The method for the treatment of tissue injury that has been caused by irradiation according to claim 1, wherein the silkworm hemolymph is obtained from the abdominal legs of a silkworm using a needle after the silkworm has fasted for 12 hours.

4. The method for the treatment of tissue injury that has been caused by irradiation according to claim 1, wherein the silkworm hemolymph is *Bombyx mori* L. silkworm hemolymph.

5. The method for the treatment of tissue injury that has been caused by irradiation according to claim 1, wherein the radiation comprises gamma ray.

6. The method for the treatment of tissue injury that has been caused by irradiation according to claim 5, wherein the wherein the silkworm hemolymph is *Bombyx mori* L. silkworm hemolymph.

* * * * *

UNITED STATES PATENT AND TRADEMARK OFFICE
CERTIFICATE OF CORRECTION

| | | |
|---|---|---|
| PATENT NO. | : 9,610,306 B2 | Page 1 of 1 |
| APPLICATION NO. | : 15/076352 | |
| DATED | : April 4, 2017 | |
| INVENTOR(S) | : Sang Hyun Park et al. | |

It is certified that error appears in the above-identified patent and that said Letters Patent is hereby corrected as shown below:

In the Claims

Column 13, Lines 27-28, "wherein the wherein the" should read -- wherein the --

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*